US005597821A

United States Patent [19]
Wolin et al.

[11] Patent Number: 5,597,821
[45] Date of Patent: Jan. 28, 1997

[54] PYRAZOLOQUINOLINES

[76] Inventors: Ronald L. Wolin, 406 Mountain Ave., Westfield, N.J. 07090; Adriano Afonso, 10 Woodmere Rd., West Caldwell, N.J. 07006

[21] Appl. No.: 356,826

[22] Filed: Dec. 15, 1994

[51] Int. Cl.$^6$ .................... A61K 31/535; C07D 487/04
[52] U.S. Cl. .................... 514/232.8; 514/236.5; 544/126
[58] Field of Search .................... 544/126; 514/232.8, 514/236.5

[56] References Cited

PUBLICATIONS

J. Biol. Chem., 261(24), 10963–65, 1986.
Nucleic Acids Research, vol. 17, No. 15(1989) pp. 6129–6141.
Townsend, Leroy, The Chemistry of Nucleosides and Nucleotides, Plenum Press, NY pp. 233–236, 1988.
JP 54157566 1979.
Chem. Lett. (1978) (6) pp. 605–608 (abstract).
J. Org. Chem. (1968) 33(5), 1806–10 (abstract).

*Primary Examiner*—Jacqueline Haley
*Assistant Examiner*—Laura R. Cross
*Attorney, Agent, or Firm*—Matthew Boxer; John J. Maitner

[57] ABSTRACT

The invention relates to compounds of the formulas

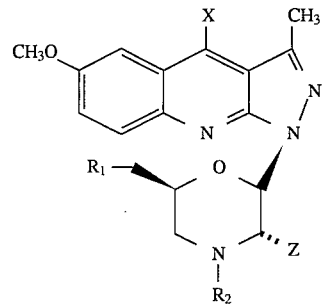

wherein $R_1$, $R_2$, X and Z are as described herein.

These compounds are useful as antitumor agents.

17 Claims, No Drawings

PYRAZOLOQUINOLINES

SUMMARY OF THE INVENTION

The invention relates to compounds of the formulas

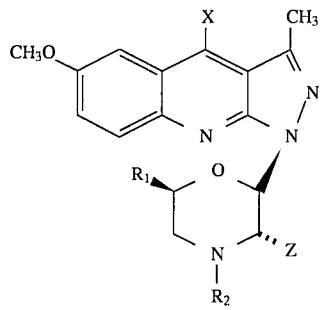
I wherein $R_1$ is $HOCH_2$; $(C_1-C_6)$-alkyl-$OCH_2$;

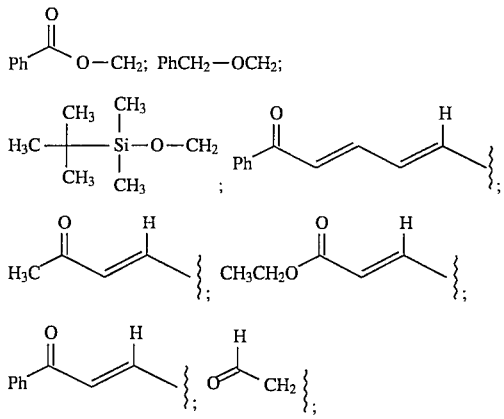

$R_2$ is H; $PhCH_2OCO$; $CH_3CH_2CO-$; $PhCH_2$; PhCO; $R_3R_4NCO-$, wherein $R_3$ and $R_4$ are each independently $C_1-C_3$ alkyl or phenyl, or taken together with the nitrogen to which they are attached are morpholine;

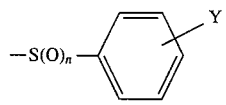

wherein n is 0, 1 or 2,
and Y is H, NHOH, Br, $NO_2$, $NHCOCH_3$;
and Z is H or CN;

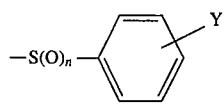

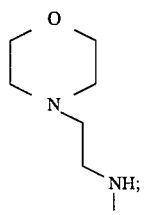

and X is H, Cl or a stereoisomer thereof, or pharmaceutically acceptable salt thereof.

Preferred are compounds of formula I wherein

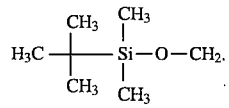

and n is 0, 1 or 2, and Y is H, NHOH, Br, $NO_2$, $NHCOCH_3$. Of these especially preferred are compounds wherein n is 2.

Also preferred are compounds of formula I wherein $R_2$ is $CH_3CH_2CO-$ or PhCO.

Also preferred are compounds of formula I wherein $R_2$ is $PhCH_2$.

Also preferred are compounds of formula I wherein $R_2$ is $PhCH_2OCO$.

Also preferred are compounds of formula I wherein $R_2$ is $R_3R_4NCO-$, and $R_3$ and $R_4$ are each independently $C_1-C_3$ alkyl or phenyl, or taken together with the nitrogen to which they are attached are Also preferred are compounds of formula I wherein $R_1$ is $HOCH_2$.

Also preferred are compounds of formula I wherein $R_1$ $$H_3C-\underset{\underset{CH_3}{|}}{\overset{\overset{CH_3}{|}}{C}}-\underset{\underset{CH_3}{|}}{\overset{\overset{CH_3}{|}}{Si}}-O-CH_2.$$

Exemplary of compounds of the invention are:

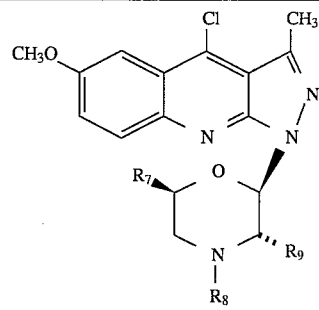

| $R_7$ | $R_8$ | $R_9$ | Biological Activity Ras p21test |
|---|---|---|---|
| $HOCH_2$ | H | H | 0% |
| $TBDMSOCH_2$ | H | H | 46% |
| $HOCH_2$ | $SO_2Ph$ | H | 12 μM |
| $TBDMSOCH_2$ | $SO_2Ph$ | H | 14 μM |
| $BzOCH_2$ | $SO_2Ph$ | H | 47% |
| $BnOCH_2$ | $SO_2Ph$ | H | 49% |
| $HOCH_2$ | $SO_2Ph$-p-$NO_2$ | H | 8 μM |
| $HOCH_2$ | $SO_2Ph$-p-NHOH | H | 22 μM |
| $HOCH_2$ | $SO_2Ph$-p-Br | H | 8.5 μM |
| $TBDMSOCH_2$ | SPh-o-$NO_2$ | H | 1 μM |
| $HOCH_2$ | SPh-o-$NO_2$ | H | 14 μM |
| PhCOCH=CH—CH=CH (trans, trans) | $SO_2Ph$-o-$NO_2$ | H | 4.8 μM |
| $TBDMSOCH_2$ | $SO_2Ph$-p-$NO_2$ | H | 5 μM |
| $HOCH_2$ | $SO_2Ph$-o-$NO_2$ | H | 14.5 μM |
| $TBDMSOCH_2$ | SPh-p-$NO_2$ | H | 50 μM |
| $HOCH_2$ | SPh-p-$NO_2$ | H | 6.7 μM |
| $TBDMSOCH_2$ | $SO_2Ph$-p-Br | H | 17.9 μM |
| $CH_3OCH_2$ | SPh-p-$NO_2$ | H | 9.0 μM |
| $TBDMSCH_2$ | $CH_2Ph$ | H | 66% |
| $HOCH_2$ | $CH_2Ph$ | H | 17% |
| $TBDMSOCH_2$ | COPh | H | 29.5 μM |
| $HOCH_2$ | COPh | H | 26% |
| PhCOCH=CH | SPh-p-$NO_2$ | H | 7.4 μM |

-continued

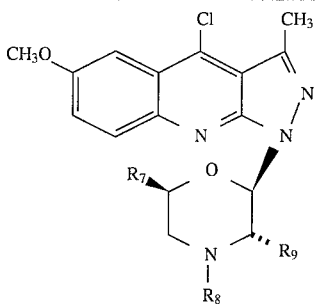

| $R_7$ | $R_8$ | $R_9$ | Biological Activity Ras p21test |
|---|---|---|---|
| EtOCOCH=CH | SPh-o-NO$_2$ | H | 16 μM |
| CH$_3$CO=CH | SPh-p-NO$_2$ | H | 88% |
| PhCOCH=CH | SO$_2$ph-p-NO$_2$ | H | 7 μM |
| EtOCOCH=CH | SO$_2$Ph-p-NO$_2$ | H | 64% |
| CH$_3$COCH=CH | SPh-o-NO$_2$ | H | 3 μM |
| PhCOCH=CH | SPh-o-NO$_2$ | H | 4.7 μM |
| PhCOCH=CH | SO$_2$Ph-p-NO$_2$ | H | 6.1 μM |
| HOCH$_2$ | H | CN | 0% |
| TBDMSOCH$_2$ | H | CN | 44% |
| HOCH$_2$ | SO$_2$Ph-p-NHCOCH$_3$ | H | 23% |
| TBDMSOCH$_2$ | SO$_2$Ph-p-NHCOCH$_3$ | H | 27 μM |
| CH$_3$COCH$_2$ | SO$_2$Ph-p-NO$_2$ | H | 9 μM |
| HOCH$_2$ | SO$_2$Ph-p-Br | H | 8.5 μM |
| TBDMSOCH$_2$ | SO$_2$Ph-p-Br | H | 7.9 μM |

Other compounds of the invention are:

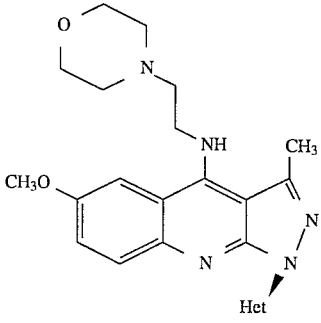

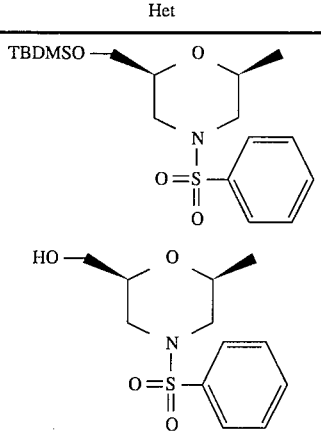

The above two compounds can be made by methods analogous to those set forth in copending application Ser. No. 08/357,624 filed Dec. 15, 1994, such as the following example from Ser. No. 08/357,624.

EXAMPLE 4

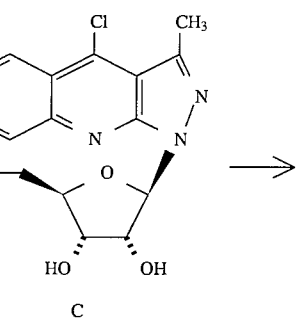

C

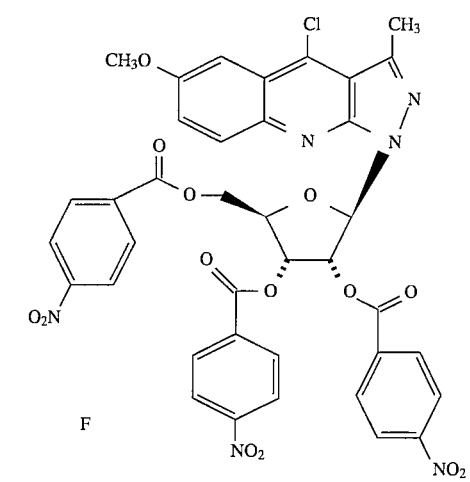

F

Procedure for preparation of the triesters w/pyrazoloquinolines:

Example for Compound F: To a pyridine solution (50 mL) of compound C (500 mg, 1.59 mmol) was added p-nitrobenzoyl chloride (1.77 g, 9.54 mmol) and DMAP (50 mg, 0.410 mmol) at room temperature The mixture was heated to 100° C. under a nitrogen atmosphere for 3 hours, then the solvent was removed under reduced pressure and the crude product was chromatographed on SiO$_2$ (2% EtOAc-Hexane) affording 1.06 g (80%) of the ribosetriester compound F.

Analytical data, MS (Cl, M+1)=534, Calc. C, 58.54; H, 3.59; N, 7.88. Found, C, 58.65; H, 3.88; N, 7.64.

Other compounds of the invention are:

| $R_{10}$ | $R_{11}$ | R' | Biological Activity Ras p 21 test |
|---|---|---|---|
| $CH_3$ | Ph | TBDMS | 28 μM |
| $CH_3$ | Ph | H | 24% |
| morpholine | | TBDMS | 60% |
| morpholine | | H | 0% |

Other compounds of the invention are:

| R | R' | Biological Activity Ras p 21 test |
|---|---|---|
| $CH_2Ph$ | TBDMS | 15 μM |
| $CH_2Ph$ | H | 59% |
| Et | TBDMS | 68% |
| Et | H | 17% |

Other exemplary compounds of the invention include:

| $R_{12}$ | $R_{13}$ | Biological Activity Ras p 21 Assay |
|---|---|---|
| $H_3C-C(CH_3)(CH_3)-Si(CH_3)(CH_3)-$ | $CH_3$ | |
| OH | $CH_3$ | 8 μM |
| TBDMS- | $-S-C_6H_4-o-NO_2$ | 1 μM |
| TBDMS | $-SO_2-C_6H_4-p-NO_2$ | |
| H | $-SO_2-C_6H_4-p-NO_2$ | 6.7 μM |
| H | H | 0% |
| TBDMS | H | 46% |
| H | $SO_2Ph$ | 12 μM |
| TBDMS | $SO_2Ph$ | 14 μM |
| Bz | $SO_2Ph$ | 47% |
| Bn | $SO_2Ph$ | 49% |
| H | $SO_2Ph$-$pNO_2$ | 8 μM |
| H | $SO_2Ph$-$pNHOH$ | 22 μM |
| H | $SO_2Ph$-$2Br$ | 8.5 μM |
| H | $SO_2Ph$-$o$-$NO_2$ | 14 μM |
| $CH_2=CHCH=CH_2Ph$ | $SO_2Ph$-$o$-$NO_2$ | 4.8 μM |

The most preferred compound of the invention is:

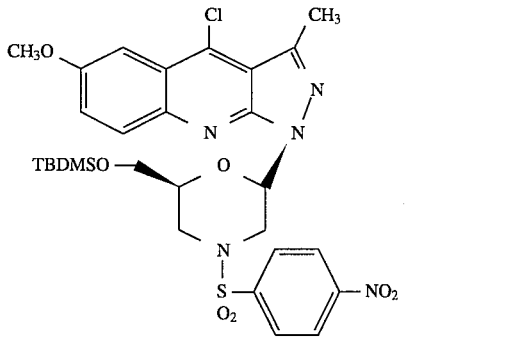

I which has an $IC_{50}$ of 5 μM in the ras p21 assay, and which has good chemical stability.

Compounds of the invention are active as agents in the treatment of tumors. Therefore, the present invention provides pharmaceutical compositions which comprise a compound of formula I and a pharmaceutically acceptable carrier therefore which compositions are useful for treating patients afflicted tumors. The present invention also provides methods of treating a patient having tumors, which methods comprise administering to said patient an anti-tumor effective amount of a compound of formula I. The present invention also provides methods for synthesizing compounds of formula I as well as other compounds of the invention.

DETAILED DESCRIPTION OF THE INVENTION

The term "$(C_1-C_8)$ alkyl" refers to straight and branched chain hydrocarbon groups of 1 to 8 carbon atoms, such as methyl, ethyl, n-, and iso-propyl, n-, sec- and tert-butyl, n-, sec-, iso-, tert- and neo-pentyl, n-, sec-,iso-, tert-hexyl and n-, sec-, iso-, tert-, and neo-heptyl and n-, sec-, iso-, tert-, and neo-octyl. The preferred $(C_1-C_8)$alkyl is methyl. Alternatively, alkyl with lower numbers of carbon atoms are also referred to in the specification. For example, the term "$(C_1-C_3)$ alkyl" refers to straight and branched chain hydrocarbon groups of 1 to 3 carbon atoms, such as methyl, ethyl, n-, and iso-propyl.

The term "$(C_1-C_8)$ alkanoyl" refers to straight and branched chain alkanoyl groups having 1 to 8 carbon atoms such as formyl, acetyl, propanoyl, butanoyl, 2-methylpropanoyl, 3-methylpropanoyl, pentanoyl, 2-methylbutanoyl, 3-methylbutanoyl, 4-methylbutanoyl, hexanoyl, 2-methylpentanoyl, 3-methylpentanoyl, 4-methylpentanoyl, 5-methylpentanoyl, heptanoyl, 3-methylheptanoyl, octanoyl, 2-ethylhexanoyl and the like. As used herein Bn refers to benzyl.

The term "halogen" refers to chlorine, fluorine, bromine, and iodine.

The term "$(C_1-C_8)$ alkoxy" refers to straight and branched chain alkoxy of 1 to 8 carbon atoms, such as methoxy, ethoxy, tert-butoxy and the like.

The term "pharmaceutically acceptable salt" refers to maleates, hydrochlorides, hydrobromides, sulfates, phosphates and tartrates. One skilled in the art will realize that acid addition salts of the compounds of the invention may be made with such salts whenever a basic functionality is present in a particular compound of the invention.

Certain compounds of this invention may exist in isomeric forms. The invention contemplates all such isomers both in pure form and in admixture, including racemic mixtures.

Certain compounds of the invention can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

The compounds of this invention can be administered in any number of conventional dosage forms, e.g., topical, oral, parenteral, rectal, transdermal, inhalation and the like. Oral or rectal dosage forms include capsules, tablets, pills, powders, cachets, and suppositories. Liquid oral dosage forms include solutions and suspensions. Parenteral preparations include sterile solutions and suspensions. Inhalation administration can be in the form of a nasal or oral spray, or by insufflation. Topical dosage forms can be creams, ointments, lotions, transdermal devices (e.g., of the conventional patch or matrix type) and the like.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, flavorings, buffers, thickeners, coloring agents, stabilizing agents, emulsifying agents, dispersing agents, suspending agents, perfumes, preservatives lubricants, etc.

Suitable pharmaceutical acceptable solid carriers are magnesium carbonate, magnesium stearate, talc, sugar, lactose, pectin, dextrin, starch, gelatin, tragacanth, methylcellulose, sodium carboxymethylcellulose, low melting waxes, cocoa butter and the like. Capsules can be made wherein the active compound is inserted into pharmaceutically acceptable capsules as a carrier. The active compounds of this invention can be mixed with pharmaceutically acceptable excipients or be used in finely divided powder form without excipients for inclusion into the capsules. Similarly, cachets are included.

Liquid form preparations include solutions, suspensions and emulsions such as water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing and thickening agents as desired. Aqueous suspensions suitable for oral use can be made by dispersing the active component in finely divided form in water with viscous material, i.e., pharmaceutically acceptable natural or synthetic gums, resins, methylcellulose, sodium carboxymethylcellulose and other well-known suspending agents.

Formulations for topical application may include the above liquid forms, as well as creams, aerosols, sprays, dusts, powders, lotions and ointments which are prepared by combining an active ingredient according to this invention with conventional pharmaceutical acceptable diluents and carriers commonly used in topical dry, liquid, cream and aerosol formulations. Ointment and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oil base and will, in general, also include one or more of pharmaceutically acceptable stabilizing agents, emulsifying agents, dispersing agents, suspending agents, thickening agents, coloring agents, perfumes and the like.

Powders may be formed with the aid of any suitable pharmaceutically acceptable powder base, e.g., talc, lactose, starch, etc. Drops may be formulated with an aqueous base or non-aqueous base also comprising one or more pharmaceutically acceptable dispersing agents, suspending agents, solubilizing agents, etc.

The topical pharmaceutical compositions may also include one or more preservatives or bacteriostatic agents, e.g., methyl hydroxybenzoate, propyl hydroxybenzoate, chlorocresol, benzalkonium chlorides, etc.

The topical pharmaceutical compositions may also contain an active compound of this invention in combination with other active ingredients such as antimicrobial agents, particularly antibiotics, anesthetics, analgesics and antipruritic agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses under conditions which retard possible decomposition. The solid form preparations intended to be converted to liquid form may contain, in addition to the active material, pharmaceutically acceptable flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of this invention may also be deliverable transdermally for systemic distribution. The transdermal compositions can take the form of creams, lotions and/or emulsions and can be included in a transdermal patch of the matrix or reservoir type as are conventional in the art for this purpose.

The compounds of this invention may be administered by any conventional mode of administration by employing an antitumor effective amount of a compound of this invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

Thus, depending on the mode, dosages of from about 0.1 to about 100 mg/kg of body weight per day may be administered to provide antitumor activity. For example, when administered orally doses of from about 20 to about 60 mg/kg of body weight may be used; and when administered parenterally, e.g., intravenously, dosages of from about 5 to about 20 mg/kg body weight may be used.

When administered topically, the amount of compound administered varies widely with the amount of skin being treated, as well as with the concentration of active ingredient applied to the affected area. Preferably, topical compositions contain from about 0.10 to about 10 percent by weight of the active ingredient and are applied as needed according to the judgment of the attending clinician. When administered rectally, the compounds of this invention may be administered in daily doses ranging from about 0.1 mg/kg to about 100 mg/kg of body weight.

The dosage to be administered and the route of administration depends upon the particular compound used, the age and general health of the patient and the severity of the tumor condition. Thus, the dose ultimately decided upon must be left to the judgment of a trained health-care practitioner.

As noted above, certain compounds of the invention are also active as anti-tumor agents. These compounds may be administered by any conventional mode of administration by employing an antitumor effective amount of a compound of the invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

Activity of the compounds of the invention can demonstrated in the assay set forth just below.

Ras p21 Nucleotide Exchange Assay

The conditions for assay of nucleotide exchange inhibitors was adapted from Hall, A. and A. J. Self. 1986 J. Biol. Chem. 261: 10963–10965, which is hereby incorporated by reference.

0.5 µM ras p21 protein was incubated in 50 µls exhange buffer (50 mM Tris-HCl pH 7.5, 5 mM $MgCl_2$, 50 mM NaCl and 10 EDTA) on ice. Compounds dissolved in dimethyl sulfoxide (DMSO) were added to the desired concentration such that the final concentration of DMSO in the reaction mixture was 2% by weight. The reaction was incubated for 5 minutes on ice and then $^3$H-GDP (final concentration was 0.25 µM) was added. The reaction was further incubated for 30 minutes at 37° C. and then stopped by addition of excess cold buffer W (10 mM Tris-HCl pH 7.5, 10mM $MgCl_2$ and 10 mM $NH_4Cl$. The ras p21 protein was collected on pure nitrocellulose filters (0.2µ pore size). The filters were washed extensively with cold buffer W and then allowed to air dry. Radioactivity on each filter was determined by scintillation counting. The amount of radioactivity bound to the filter is a direct measure of the amount of $^3$H-GDP bound to p21 ras. The extent to which a compound inhibited the exchange reaction was determined by comparing the amount of $^3$H-GDP bound to the ras p21 protein in the presence of that compound versus the amount of $^3$H-GDP bound to the ras p21 protein in the absence of that compound.

Activity of the compounds of the invention in the assay set forth just above indicates that the compounds of the invention have activity as anti-tumor agents. More specifically, inhibition of the binding of $^3$H-GDP to the ras p21 protein by a compound, indicates that the compound has activity as an antitumor agent.

Biological data are given throughout the specification in one of two forms: either as percent inhibitions, or as the concentration at which the test compound causes 50% inhibition ($IC_{50}$) of the binding of $^3$H-GDP to the ras p21 protein.

When the above assay was run at one concentration of the test compound, then the data was given as percent inhibition. When the assay was run at a series of concentrations, then the data were given as $IC_{50}$'s.

What follows is a description showing how the compounds of the invention are made.

Unless otherwise noted, all reactions were run under an inert atmosphere such as nitrogen. Most chromatographies were started by dissolving the reaction residue in the more polar solvent to keep it homogeneous for loading.

REACTION SCHEME 1

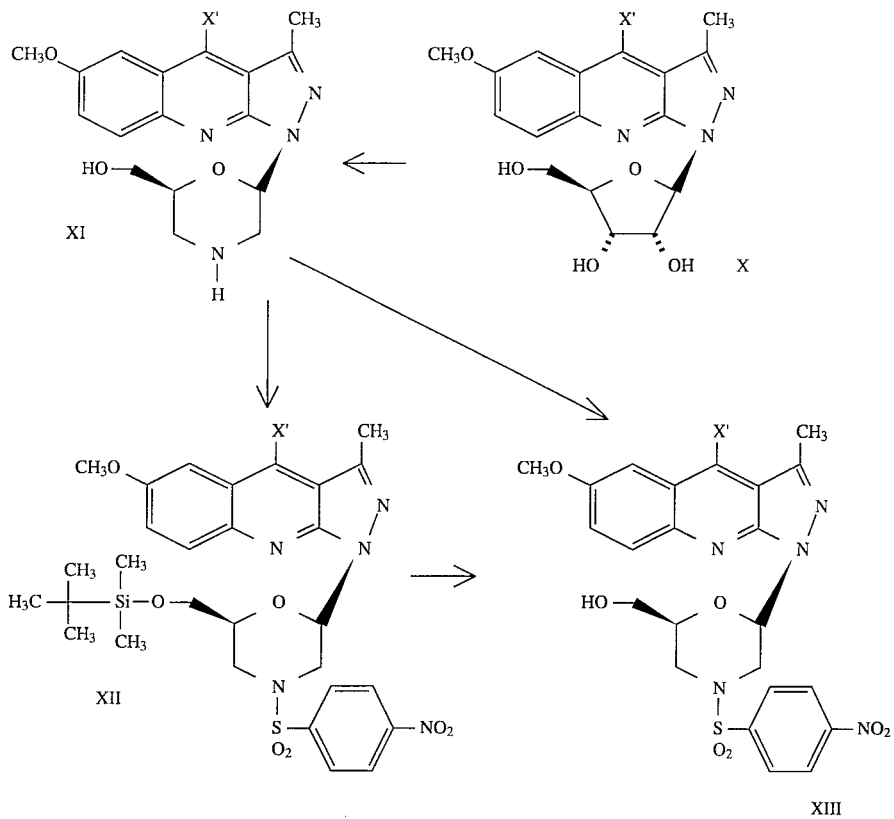

wherein X' is H or Cl.

A compound of formula X may be prepared as described in copending application Ser. No. 08/357,624 filed Dec. 15, 1994, such as the following example from Ser. No. 08/357,624.

EXAMPLE 2

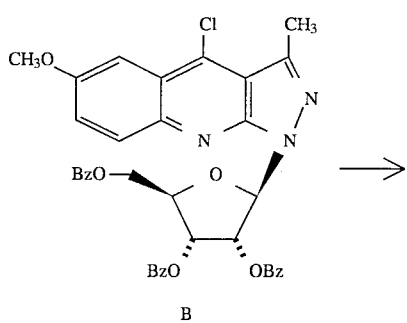

B

-continued

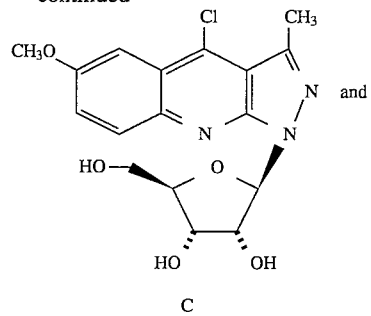

C and

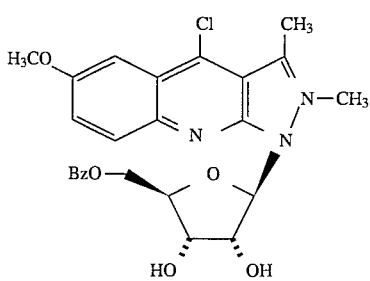

D

Procedure for hydrolysis w/ammonia:

Example for Compounds C and D: To compound B was added a saturated solution of methanolic ammonia. The mixture was stirred at room temperature for 3 days in a stoppared flask. SiO$_2$ was then added to the mixture and the solvent was evaporated under reduced pressure. Purification by flash chromatography on SiO$_2$ (MeOH—CH$_2$Cl$_2$) provided the C5'-monobenzoate, compound D and the triol, compound C in ratios that varied from experiment to experiment. Use of NaOMe as shown in Example 3 below, provided only the triol compound C.

Analytical data for compound D (CI, M+1)=484, MP=230–232, Calc. C, 59.57; H, 4.58; N, 8.68. Found, C, 59.68; H, 4.56; N, 8.64. Analytical data for compound C, MS (CI, M+1)=380, MP=198–200, Calc. C, 53.76; H, 4.78; N, 11.06; Cl, 9.33. Found C, 53.67; H, 4.69; N, 10.83; Cl, 9.19.

A compound of formula X may be reacted with an oxidizing agent agent such as Pb(OAc)$_4$ or more preferably NaIO$_4$ in a polar solvent such as water, methanol, acetonitrile or EtOH:H$_2$O:CH$_2$Cl$_2$ (300:60:150 v/v/v) at a temperature in the range of about 0° to about 25° C. most preferably about room temperature for about 3 to about 5 hours most preferably 3.5 hours. The secodialdehyde which is formed can be dissolved in a polar solvent such as water, methanol, acetonitrile or EtOH:H$_2$O: CH$_2$Cl$_2$ (300:60:150 v/v/v) at a temperature in the range of about 0° to about 25° C., most preferably about room termperature. To this solution is added a nitrogen source such as ammonium carbonate, or more preferably ammonium biborate, (NH$_4$)$_4$B$_2$O$_7$, at about room temperature. The reaction mixture is stirred between about ½ to about 3 hours, preferably 2½ hours, then a reducing agent such as NaBH$_4$ or more preferably NaBH$_3$CN is added and the reaction is allowed to stir for about 20 to 120 minutes. The resulting compound of formula XI may be recovered by conventional isolation techniques. The above reaction ribose compound to the morpholine compound may be carried in accordance weith techniques set forth in Nucleic Acid Research (1989), 6129 D. Weller et al, which is hereby incorporated by reference.

A compound of formula XI may be converted to a compound of formula XII by adding the protecting group TBDMS as shown in the examples below.

A compound of formula XI may be reacted with an acylating agent such a sulfenyl chloride, a substituted benzenesulfonyl chloride such as p-nitro, p-bromo, p-chloro or benzensulfonylchloride, or toluene; most preferably p-nitrobenzensulfonyl chloride, in a nonpolar solvent such as 1,2-dichloroethane, or more preferably dichloromethane containing a base such as pyridine, collidine, lutidine or more preferably Et$_3$N, p-nitrosulfonylchloride at a temperature in the range of about −10° to about 25° C. most preferably about −5° C., for about 1 to 4 hours preferably about 1 hours. Conventional workup will yield a compound of formula XIII.

A compound of formula XI may be reacted with a sulfenyl chloride reagent such as benzene sulfenyl chloride or more preferably p-nitrosulfenyl chloride in an aprotic solvent such as dichloroethane, pyridine, or CH$_2$Cl$_2$ in the presence of a base such as pyridine, collidine or more preferably Et$_3$N at a temperature in the range of about 0° to about 35° C. most preferably about room temperature for about 1 to about 6 hours most preferably about 3 hours. Silica gel chromatography will yield a compound of formula XX.

Sulfenyl compounds which are commercially available include 2-nitro-4-carboxy phenyl sulfenyl chloride; 4-nitrobenzenesulfenyl chloride; 2,4-dinitrobenzenesulfenylchloride; 2-nitrobenzenesulfenyl chloride; and benzene sulfenyl chloride. Compounds may also be prepared according to literature methods such as Hopkins et al, J Org Chem. 43, p1208, (1978) and Harpp et al, J Org Chem. 43, p3481, (1978) and Marcuzzi et al Synthesis, p.451, (1976) which are hereby incorporated by reference.

All other compounds of the invention may be synthesized by methods shown in the examples below, or they may be synthesized by methods analogous to those set forth in the examples below or in the literature cited herein.

EXAMPLES

Example 1

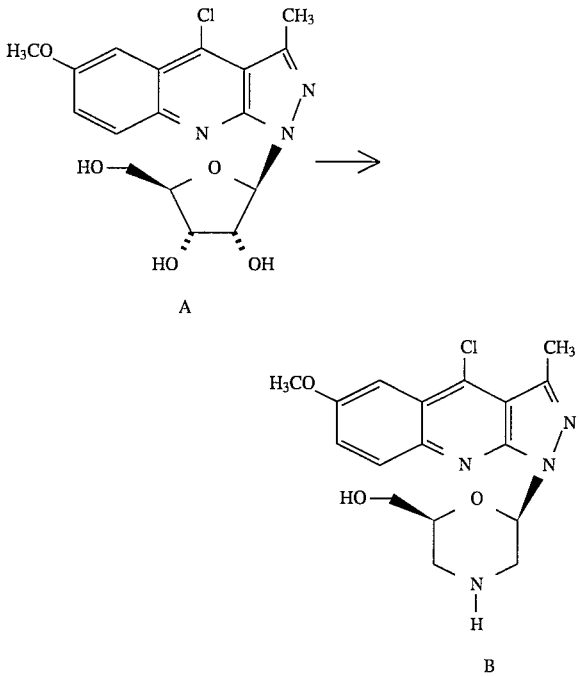

Procedure for formation of the morpholine subunit:

For the preparation of compound B: To a EtOH:H$_2$O:CH$_2$Cl$_2$ (300:60:150 v/v/v) solution of compound A was added NaIO$_4$ (9.95 g, 46.7 mmol) at room temperature. A cloudy precipitate began to form after 10 minutes, and after 3.5 hours the reaction was judged to be complete by thin layer chromatography (tlc). SiO$_2$ (20 g) was added and the mixture was evaporated to dryness under reduced pressure. The adsorbed material was chromatographed on SiO$_2$ using (5% MeOH:CH$_2$Cl$_2$) which afforded 8.1 g of the secodialdehyde as a stable amorphous yellow solid. To a rapidly stirring MeOH:CH$_2$Cl$_2$ (50:20 v/v) solution of the secodialdehyde (1.0 g, 2.65 mmol), was added (NH$_4$)$_4$B$_2$O$_7$ (0.770 g, 2.92 mmol) at room temperature. After the mixture stirred for 2.5 hours, NaBH$_3$CN (0.170 g, 2.70 mmol) was introduced and stirring was continued for another 20 minutes. SiO$_2$ (5 g) was added and the contents were evaporated to dryness.

Chromatography on SiO$_2$ using (5% MeOH:CH$_2$Cl$_2$) provided 0.603 g (62%) of the morpholine product, compound B and approximately 0.400 g (~40%) of the nitrile adduct.

Analytical data for compound B is as follows: MS (CI, M+1)=363, mp=220 (dec). Analytical data for, MS (CI, M+1)=388, mp=193–196, Calc. C, 55.75; H, 4.68; N, 18.06. Found. C, 55.94; H, 4.74; N, 17.67.

Example 2

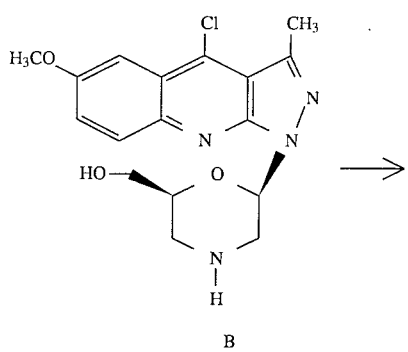

B

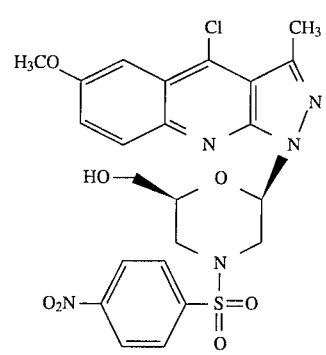

C

Procedure for derivatization of the morpholine nitrogen:

For preparing compound C: A 2-necked flask containing compound B (2.0 g, 5.52 mmol) in CH$_2$Cl$_2$ (60 mL) was fitted with two pressure equalizing dropping funnels. One dropping funnel contained Et$_3$N (800 μL in 10 mL CH$_2$Cl$_2$) and the other dropping funnel contained p-nitrosulfonyl-chloride (1.35 g, 6.09 mmol, in 10 mL CH$_2$Cl$_2$). The contents of each dropping funnel were added slowly to compound B at –5° C. After 1 hour the reaction was judged to be complete by tlc and the solvents were removed under reduced pressure and the residue was chromatographed on SiO$_2$ using (5% EtOAc—CH$_2$Cl$_2$) which provided 1.66 g (55%) of compound C and 80 mg (2%) of the bis-addition product. Employing this protocol eliminates having to first protect the C5' alcohol.

Analytical data for compound C is as follows: MS (CI, M+1)=548, mp=158 (dec).

Example 2a

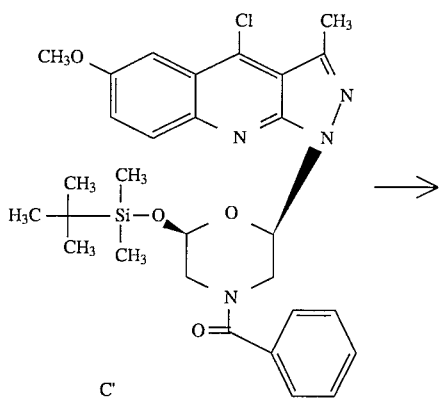

C'

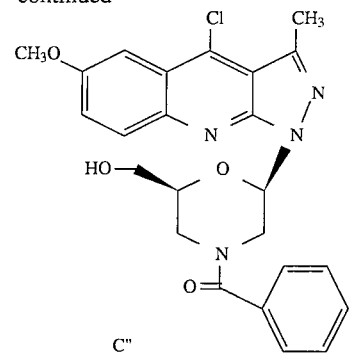

C"

To a solution of compound C' (270 mg) was added 1 mL of a 2.5M HF/CH$_3$CN solution at room temperature. After 1 hour another 1 mL aliquot of HF/CH$_3$CN was introduced. After stirring for a total of 2 hours, the contents were evaporated and the residue was chromatographed on silica gel (12% MeOH—CH$_2$Cl$_2$) yielding compound C" as a yellow solid, 197 mg (90%) (MS,FAB: M+H=467).

Example 3

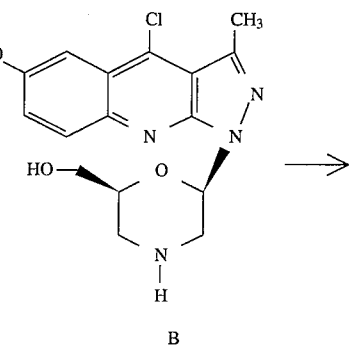

B

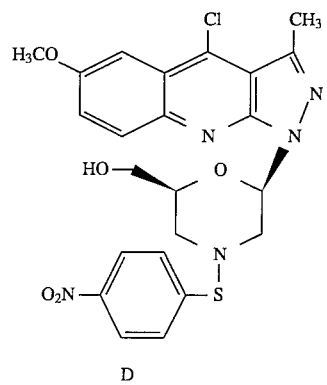

D

Example for compound D: To a flask containing compound B, (5.5 g, 15.2 mmol) in CH$_2$Cl$_2$ (250 mL) was added Et$_3$N (2.27 g, 22.5 mmol) followed by p-nitrosulfenyl chloride (3.5 g, 18.2 mmol) at room temperature. After 3 hours, the solvent was evaporated and the residue was chromatographed on SiO$_2$ using (3% MeOH—CH$_2$Cl$_2$) giving 3.52 g (45%) of compound D as a yellow solid.

Analytical data, MS (CI, M+1)=516, m.p.=100°–107° C. Calc. C, 53.54; H, 4.29; N, 13.54. Found, C, 53.43; H, 4.33; N, 13.16.

17
Example 4

18
Example 5

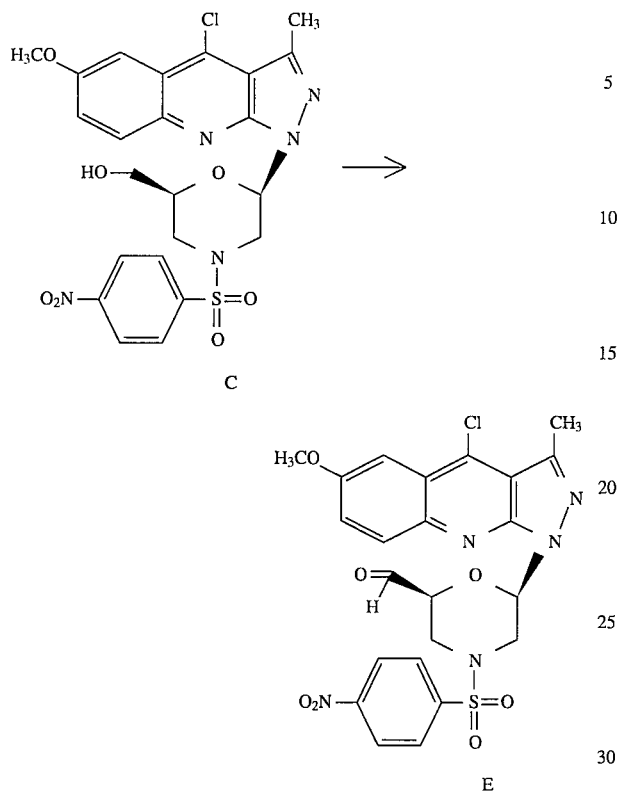

General procedure for the Dess-Martin Oxidation:

Example for compound E: To a CHCl$_3$ (70 mL) solution of compound C (340 mg, 0.620 mmol) was added the Dess-Martin reagent (316 mg, 745 mmol) at room temperature. After 2 hours, more of the Dess-Martin reagent was added (316 mg) and stirring was continued for another 2 hours. The solvent was evaporated under reduced pressure and the residue was chromatographed on SiO$_2$ using (20%-EtOAc—CH$_2$Cl$_2$) which afforded 250 mg (73%) of the aldehyde, compound E. The Moffatt oxidation of the C5' alcohol did not work in the morpholine sulfonamide series.

Analytical data for compound E is as follows

MS (CI, M+1)=546.

The Dess-Martin oxidation above was done according to procedures described in, or analogous to those of the following two publications: Dess, J. C. Martin: J. Org. Chem. 4156 (1983); and R. E. Ireland, L. Liu; J. Org. Chem. 2899 (1993). These just above two publications are hereby incorporated by reference.

To a CH$_2$Cl$_2$ (100 ml) solution of compound B (4.55 g, 12.57 mmol) at room temperature was added imidazole (2.22 g, 32.68 mmol) followed by the addition of TBDMSCI (2.46g, 16.34mmol). The reaction mixture became quite viscous after a short while and was diluted with an additional 100 mL of CH$_2$Cl$_2$. The reaction mixture was stirred at room temperature for 1.5 hours, then the solvents were removed under reduced pressure, and the residue was chromatographed on silica gel (5% acetone-CH$_2$Cl$_2$, increasing to 5% acetone-2% MeOH—CH$_2$Cl$_2$ which afforded 4.24 g (70%) of the silylether compound B". The analytical data for this compound is as follows: MS, FAB, (M+H=477).

Example 6

19
-continued

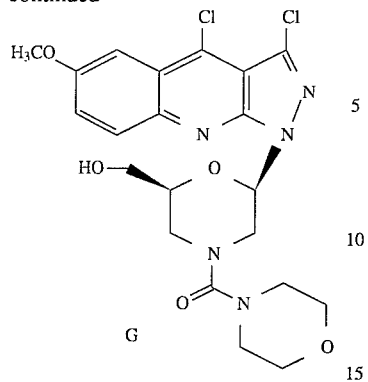

G

To an acetonitrile solution of compound F was added a 2.5M HF/CH₃CN solution (1 mL) at room temperature. After 1 hour, a second aliquot of HF/CH₃CN was introduced. After a total of 3 hours, the solvents were removed in vacuo and the residue was chromatographed on silica gel (5% MeOH—CH₂Cl₂) to yield 123 mg (76%) of the alcohol product as compound G as a yellow solid. MS, SIMS, (M+H=476.2)

Example 7

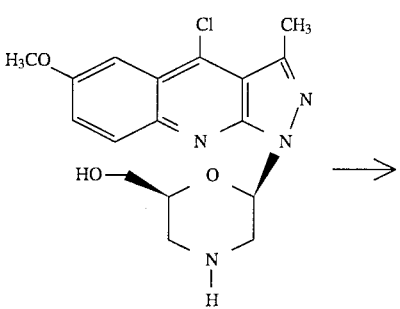

B

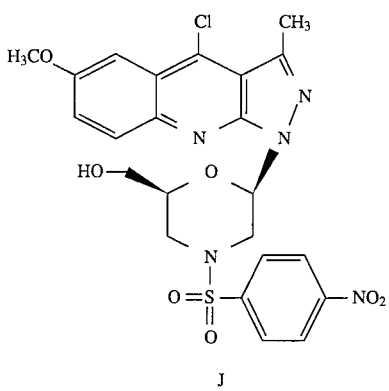

J

A 2-necked flask containing compound B (2.0 g, 5.52 mmol) in CH₂Cl₂ (60 mL) was fitted with two pressure equalizing dropping funnels. One dropping funnel contained Et₃N (800 μl in 10 mL CH₂Cl₂) and the other dropping funnel contained p-nitrosulfonylchloride (1.35 g, 6.09 mmol, in 10 mL CH₂Cl₂). The contents of each dropping funnel were added slowly to compound B at −5° C. After 1 hour, the reaction was judged to be complerte by tlc and the solvents were removed under reduced presuure and the residue was chromatographed on SiO₂ using (5% EtOAc—

20

CH₂Cl₂) which provided 1.66 g (55%) of compound J and 80 mg (2%) of the bis-addition product. Enmploying this protocol eliminates having to first protect the C5' alcohol.

Analytical data for the compound J is as follows: 54365 MS(CI, M+1)=548 mp is 158° C. (dec).

What is claimed is:

1. A compound of the formula:

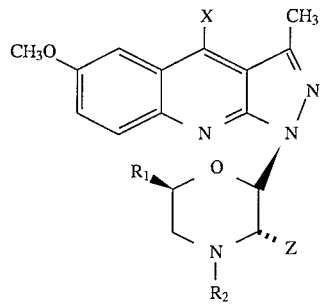

I wherein R₁ is HOCH₂; (C₁–C₆)-alkyl-OCH₂;

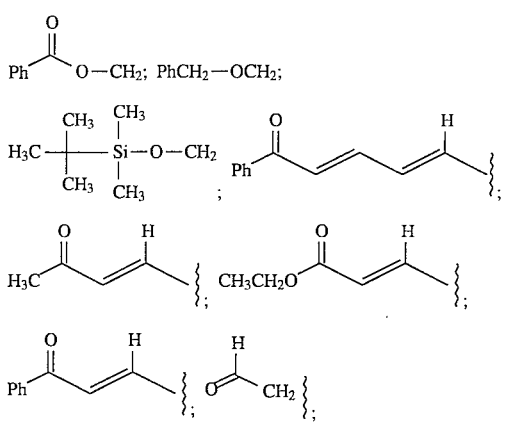

R₂ is H; PhCH₂OCO; CH₃CH₂CO—; PhCH₂; PhCO;; R₃R₄NCO—, wherein R₃ and R₄ are each independently C₁–C₃ alkyl or phenyl, or taken together with the nitrogen to which they are attached are morpholine;

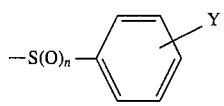

wherein n is 0, 1 or 2,
Y is H, NHOH, Br, NO₂, NHCOCH₃;
Z is H or CN;

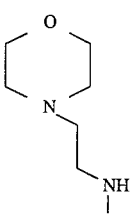

X is H, Cl, or a stereoisomer thereof, or pharmaceutically acceptable salt thereof.

2. A compound according to claim 1 wherein $R_2$ is

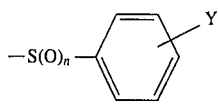

and n is 0, 1 or 2, and Y is H, NHOH, Br, $NO_2$, $NHCOCH_3$.

3. A compound according to claim 2 wherein n is 2.

4. A compound according to claim 1 wherein $R_2$ is $CH_3CH_2CO-$ or PhCO.

5. A compound according to claim 1 wherein $R_2$ is $PhCH_2$.

6. A compound according to claim 1 wherein $R_2$ is $PhCH_2OCO$.

7. A compound according to claim 1 wherein $R_2$ is $R_3R_4NCO-$, wherein $R_3$ and $R_4$ are each independently $C_1-C_3$ alkyl or phenyl.

8. A compound according to claim 1 wherein $R_1$ is $HOCH_2$.

9. A compound according to claim 1 wherein $R_1$ is

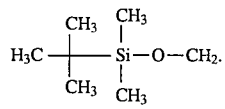

10. A compound selected from the group consisting of

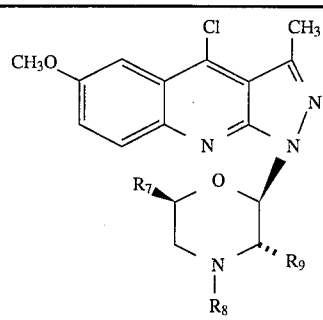

| $R_7$ | $R_8$ | $R_9$ |
|---|---|---|
| $HOCH_2$ | H | H |
| $TBDMSOCH_2$ | H | H |
| $HOCH_2$ | $SO_2Ph$ | H |
| $TBDMSOCH_2$ | $SO_2Ph$ | H |
| $BzOCH_2$ | $SO_2Ph$ | H |
| $BnOCH_2$ | $SO_2Ph$ | H |
| $HOCH_2$ | $SO_2Ph$-p-$NO_2$ | H |
| $HOCH_2$ | $SO_2Ph$-p-NHOH | H |
| $HOCH_2$ | $SO_2Ph$-p-Br | H |
| $TBDMSOCH_2$ | SPh-o-$NO_2$ | H |
| $HOCH_2$ | SPh-o-$NO_2$ | H |
| PhCOCH=CH—CH=CH— (trans, trans) | $SO_2Ph$-o-$NO_2$ | H |
| $TBDMSOCH_2$ | $SO_2Ph$-p-$NO_2$ | H |
| $HOCH_2$ | $SO_2Ph$-o-$NO_2$ | H |
| $TBDMSOCH_2$ | SPh-p-$NO_2$ | H |
| $HOCH_2$ | SPh-p-$NO_2$ | H |
| $TBDMSOCH_2$ | $SO_2Ph$-p-Br | H |
| $CH_3OCH_2$ | SPh-p-$NO_2$ | H |
| $TBDMSOCH_2$ | CH2Ph | H |
| $HOCH_2$ | CH2Ph | H |
| $TBDMSOCH_2$ | COPH | H |
| $HOCH_2$ | COPH | H |
| PhCOCH=CH | SPh-p-$NO_2$ | H |
| EtOCOCH=CH | SPh-o-$NO_2$ | H |
| $CH_3COCH=CH$ | SPh-p-$NO_2$ | H |

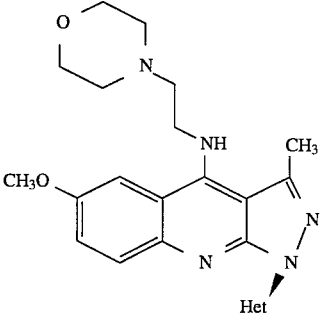

| $R_7$ | $R_8$ | $R_9$ |
|---|---|---|
| PhCOCH=CH | $SO_2Ph$-p-$NO_2$ | H |
| EtOCOCH=CH | $SO_2Ph$-p-$NO_2$ | H |
| $CH_3COCH=CH$ | SPh-o-$NO_2$ | H |
| PhCOCH=CH | SPh-o-$NO_2$ | H |
| PhCOCH=CH | $SO_2Ph$-m-$NO_2$ | H |
| $HOCH_2$ | H | CN |
| $TBDMSOCH_2$ | H | CN |
| $HOCH_2$ | $SO_2Ph$-p-$NHOCH_3$ | H |
| $TBDMSOCH_2$ | $SO_2Ph$-p-$NHOCH_3$ | H |
| $CH_3COCH_2$ | $SO_2Ph$-p-$NO_2$ | H |
| $HOCH_2$ | $SO_2Ph$-p-Br | H |
| $TBDMSOCH_2$ | $SO_2Ph$-p-Br | H | or a pharmaceutically acceptable salt thereof.

11. A compound according to claim 1 selected from the group consisting of

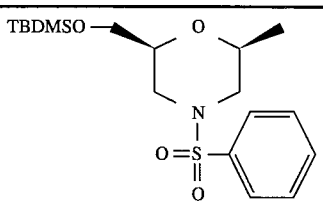

Het

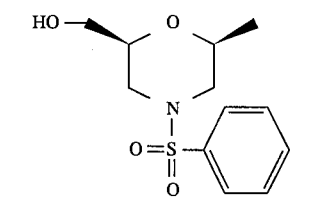

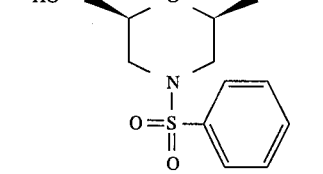

or a pharmaceutically acceptable salt thereof.

12. A compound according to claim 1 selected from the group consisting of

[Structure: quinoline-pyrazole fused ring system with CH₃O, Cl, CH₃ substituents, and morpholine-type ring bearing R'O— and N—C(O)—N(R₁₀)(R₁₁)]

| R₁₀ | R₁₁ | R' |
|---|---|---|
| CH₃ | Ph | TBDMS |
| CH₃ | Ph | H |
| morpholine | | TBDMS |
| morpholine | | H |

13. A compound selected from the group consisting of

[Structure: quinoline-pyrazole fused ring system with CH₃O, Cl, CH₃ substituents, and morpholine ring bearing R'O— and N—C(O)—OR]

| R | R' |
|---|---|
| CH₂Ph | TBDMS |
| CH₂Ph | H |
| Et | TBDMS |
| Et | H | or a pharmaceutically acceptable salt thereof.

14. A compound selected from the group consisting of

[Structure: quinoline-pyrazole fused ring system with CH₃O, Cl, CH₃ substituents, and morpholine ring bearing R₁₂O— and N—R₁₃]

| R₁₂ | R₁₃ |
|---|---|
| H₃C—C(CH₃)₂—Si(CH₃)₂— (TBDMS) | CH₃ |
| OH | CH₃ |

-continued

[Structure: same core with R₁₂O— and N—R₁₃]

| R₁₂ | R₁₃ |
|---|---|
| TBDMS | —S—(2-O₂N-C₆H₄) |
| TBDMS | —SO₂—(4-NO₂-C₆H₄) |
| H | —SO₂—(4-NO₂-C₆H₄) |
| H | H |
| TBDMS | H |
| H | SO₂Ph |
| TBDMS | SO₂Ph |
| Bz | SO₂Ph |
| Bn | SO₂Ph |
| H | SO₂Ph-pNO₂ |
| H | SO₂Ph-pNHOH |
| H | SO₂Ph-pBr |
| TBDMS | SO₂Ph-o-NO₂ |
| H | SO₂Ph-o-NO₂ |
| CH₂=CHCH=CH₂Ph | SO₂Ph-o-NO₂ | or a pharmaceutically acceptable salt thereof.

15. The compound according to claim 1 having the formula

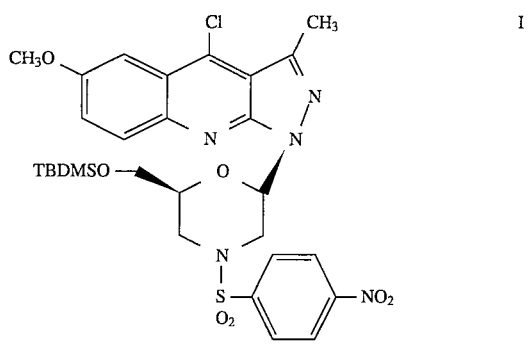

I or a pharmaceutically acceptable salt thereof.

16. A composition comprising an antitumor effective amount of a compound according to claim 1 and a pharmaceutically acceptable carrier material, with the proviso that the compound according to claim 1 is not the compound of formula I wherein X is Cl, R₁ is HOCH₂, R₂ is H, and Z is H.

17. A method for treating a tumor, wherein said tumor is treatable by a compound according to claim 1 which inhibits the binding of $^3$H-GDP to the ras p21 protein, which comprises administering an antitumor effective amount of said compound to a mammal in need thereof.

* * * * *